United States Patent
Bani-Hashemi et al.

(10) Patent No.: US 8,582,719 B2
(45) Date of Patent: *Nov. 12, 2013

(54) SYSTEM AND METHOD FOR TOMOSYNTHESIS

(75) Inventors: Ali Bani-Hashemi, Walnut Creek, CA (US); Jonathan Maltz, Oakland, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 86 days.

This patent is subject to a terminal disclaimer.

(21) Appl. No.: 13/081,441

(22) Filed: Apr. 6, 2011

(65) Prior Publication Data

US 2011/0176655 A1    Jul. 21, 2011

Related U.S. Application Data

(63) Continuation of application No. 12/045,530, filed on Mar. 10, 2008, now Pat. No. 7,936,858.

(60) Provisional application No. 60/995,828, filed on Sep. 28, 2007.

(51) Int. Cl.
A61B 6/02    (2006.01)
A61B 6/00    (2006.01)

(52) U.S. Cl.
USPC ............................................. 378/65; 378/21

(58) Field of Classification Search
USPC ........ 378/21–27, 65, 119, 121, 122, 124, 134
See application file for complete search history.

(56) References Cited

U.S. PATENT DOCUMENTS

| | | | |
|---|---|---|---|
| 4,736,396 A * | 4/1988 | Boyd et al. ...................... 378/4 |
| 4,998,268 A * | 3/1991 | Winter .............................. 378/63 |
| 5,751,781 A * | 5/1998 | Brown et al. .................... 378/65 |
| 6,710,362 B2 | 3/2004 | Kraft et al. |
| 7,221,733 B1 | 5/2007 | Takai et al. |
| 7,227,925 B1 * | 6/2007 | Mansfield et al. .............. 378/65 |
| 7,245,698 B2 * | 7/2007 | Pang et al. ...................... 378/65 |
| 7,519,151 B1 * | 4/2009 | Shukla et al. ................... 378/65 |
| 7,711,087 B2 * | 5/2010 | Mostafavi ....................... 378/65 |
| 7,848,488 B2 * | 12/2010 | Mansfield ....................... 378/65 |

(Continued)

FOREIGN PATENT DOCUMENTS

WO    WO 2007/038306    4/2007

OTHER PUBLICATIONS

Written Opinion dated Nov. 25, 2010 in counterpart EP application No. 08 834 905.5-2319, 4 pages.

(Continued)

*Primary Examiner* — Anastasia Midkiff

(57) ABSTRACT

A system and method for tomosynthesis, the method including emitting a respective imaging x-ray from each of a plurality of imaging x-ray sources disposed in a fixed relation with respect to one another, acquiring x-ray absorption projections of an object, each of the x-ray absorption projections associated with an imaging x-ray emitted by a respective one of the plurality of imaging x-ray sources, and performing digital tomosynthesis using the x-ray absorption projections to generate a cross-sectional image of the object.

11 Claims, 8 Drawing Sheets

(56) References Cited

U.S. PATENT DOCUMENTS

| | | | |
|---|---|---|---|
| 2006/0067468 A1 | 3/2006 | Rietzel et al. | |
| 2007/0167748 A1 | 7/2007 | Rietzel | |
| 2007/0269000 A1* | 11/2007 | Partain et al. | 378/37 |
| 2007/0280408 A1* | 12/2007 | Zhang | 378/10 |
| 2007/0291895 A1* | 12/2007 | Yin et al. | 378/20 |
| 2008/0273659 A1* | 11/2008 | Guertin et al. | 378/65 |
| 2009/0086909 A1* | 4/2009 | Hui et al. | 378/65 |
| 2009/0279662 A1 | 11/2009 | Rietzel | |

OTHER PUBLICATIONS

Zhang, J. et al., *Multiplexing radiography using a carbon nanotube based x-ray source*, Applied Physics Letters, AIP, American Institute of Physics, Melville, NY US; vol. 89, No. 6, Aug. 9, 2006; pp. 64106-064106-3.

Enghardt, et al., *Charged hadron tumour therapy monitoring by means of PET*; 2004, Nuclear Instruments and Methods in Physics Research A 525 (2004); pp. 284-288.

\* cited by examiner

SYSTEM AND METHOD FOR TOMOSYNTHESIS

CROSS-REFERENCE TO RELATED APPLICATIONS

The present application claims priority to U.S. Provisional Patent Application No. 60/995,828, filed on Sep. 28, 2007 and entitled "Online IGRT Using Digital Tomosynthesis", and is a continuation of U.S. patent application Ser. No. 12/045,530, filed on Mar. 10, 2008 entitled, "System and Method for Tomosynthesis," the contents of which are incorporated herein by reference for all purposes.

BACKGROUND

It is often desirable to reconstruct images of structures existing within an imaged object from a set of projection radiographs. In medical applications, anatomical structures such as organs, blood vessels and bones may be imaged.

Prior systems for providing such images have commonly utilized computed tomography (CT) technology. In CT, both an x-ray source and an x-ray detector move on a circular path around a common axis, and a very high number of projection radiographs (or images) are acquired.

In contrast, in tomosynthesis processes, relatively few radiographs are acquired for varying x-ray source positions. Typically the x-ray source assumes positions that are essentially on one side of the object, while the detector (or film) assumes positions on the opposite side of the object.

Digital tomosynthesis (DT) is a method of reconstructing cross sections of a 3D body from its 2D radiographic projections, which is a much faster method than the CT approach for obtaining cross sections. In CT, projections must be acquired from at least 180 degrees plus the fan angle around the object to produce an exact reconstruction of the object. DT, however, exploits projections from limited angles to reconstruct cross sections of the object.

Although the reconstruction is less precise and the plane of reconstruction is limited to one orientation only, DT has the benefit of using a smaller number of projections. This translates into faster data acquisition and provides the advantage of being able to reconstruct objects where space and size limitations prevent one from acquiring projections from all angles. In some clinical situations, exact reconstruction is not necessary, making a fast DT ideal.

Generally, DT image acquisition, reconstruction and readout are carried out by a processing unit such that the time required for such processes is limited. Imaging time depends on detecting a quantum of photons and is therefore a function of both the efficiency of the image screens as well as the allowable signal-to-noise ratio. Conventional image detection screens can produce images with a rate of 15-30 images per second. The time required to acquire an image is generally a function of several factors including the readout time for the image detector, required duration of exposure to generate an image and the heat dissipation capabilities of the x-ray source. The time required for the image acquisition can be reduced by using more efficient imaging screens so as to increase the imaging capacities thereby reducing the amount of radiation required and limiting exposure times. Similarly, DT reconstruction may be accelerated by special purpose hardware making its contribution to the overall process timing negligible.

The image processing and reconstruction time may be reduced by increasing the compute power. The image processing and reconstruction time could be made to be relatively minor compared to the total time. The imaging time will be primarily a function of the mechanical movement required to position the x-ray source relative to the object to be imaged.

Therefore, it would be desirable to provide a DT system and method which, in some embodiments, may result in reduced imaging times.

SUMMARY

Some embodiments concern a plurality of imaging x-ray sources disposed in a fixed relation with respect to one another, each of the plurality of imaging x-ray sources to emit a respective imaging x-ray, an x-ray detector to acquire x-ray absorption projections of an object, each of the x-ray absorption projections associated with an imaging x-ray emitted by a respective one of the plurality of imaging x-ray sources, and a processor to perform digital tomosynthesis using the x-ray absorption projections to generate a cross-sectional image of the object.

Some aspects may comprise emission of a respective imaging x-ray from each of a plurality of imaging x-ray sources disposed in a fixed relation with respect to one another, acquisition of x-ray absorption projections of an object, each of the x-ray absorption projections associated with an imaging x-ray emitted by a respective one of the plurality of imaging x-ray sources, and performance of digital tomosynthesis using the x-ray absorption projections to generate a cross-sectional image of the object.

BRIEF DESCRIPTION OF THE DRAWINGS

The numerous objects and advantages of some embodiments may be better understood by those in the art by reference to the accompanying figures in which.

DETAILED DESCRIPTION

Figure 1:
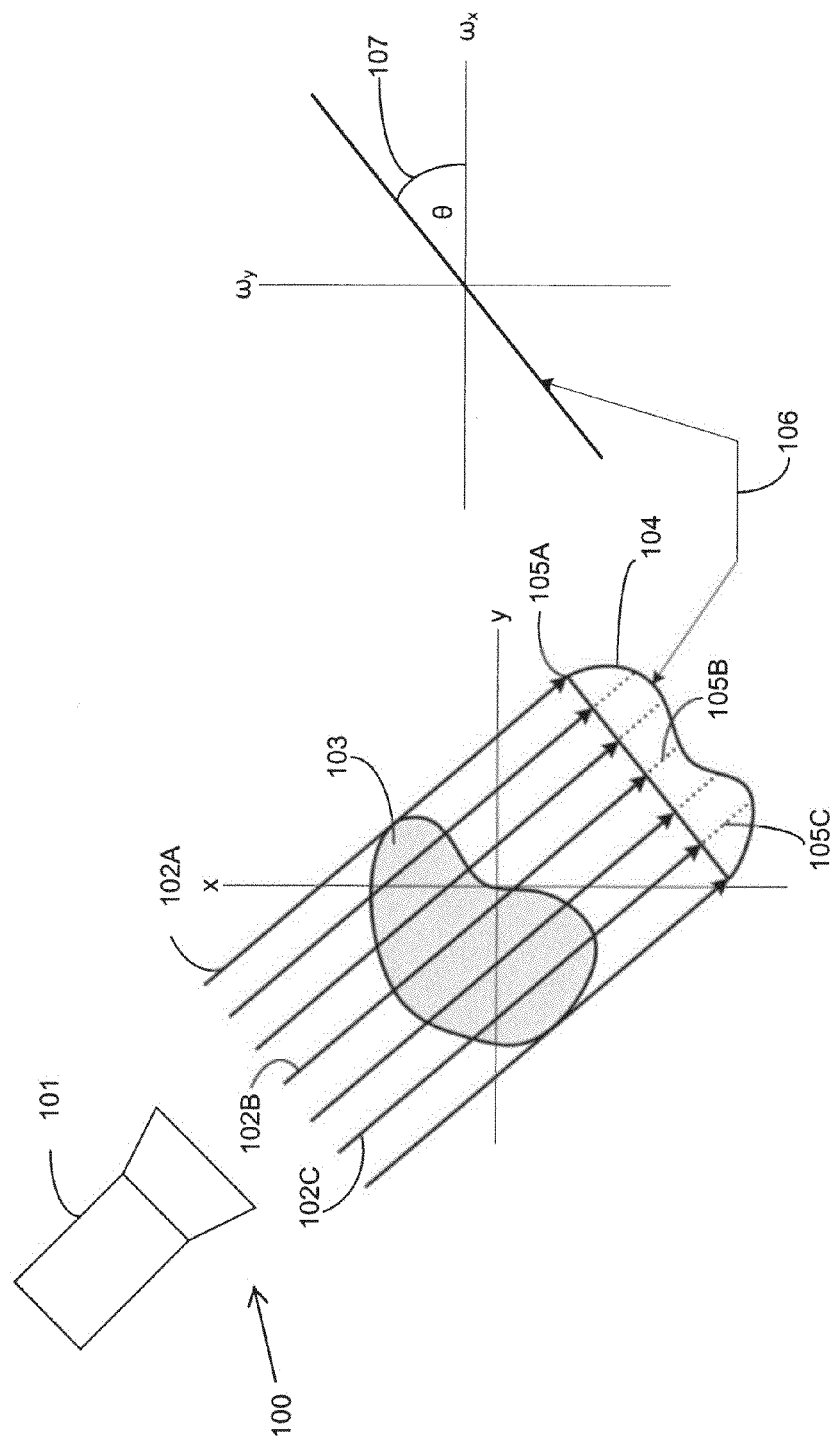
FIG. 1 depicts the operation of an x-ray system.

The following discussion is presented to enable a person in the art to make and use the present teachings. Various modifications to the illustrated embodiments will be readily apparent to those in the art, and the generic principles herein may be applied to other embodiments and applications without departing from the present teachings. Thus, the present teachings are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present teachings.

Referring to FIG. 1, the general operation of an x-ray system 100 is presented. An x-ray source 101 may produce a parallel set of x-rays 102 which project through an object 103, thereby resulting in an x-ray absorption projection 104. Each point on the absorption projection 104 constitutes the line integral 105 of the x-ray absorption along a corresponding ray 102. For example, the absorption of rays 102A, 102B and 102C, may result in line integral values 105A, 105B, and 105C respectively (each having a progressively greater integral value due to the thickness of the object 103).

According to the Projection-Slice Theorem, the Fourier transform 106 of a projection 104 corresponds to the cross-sectional slice of the Fourier transform of the object 103 which intersects the origin having an angle θ 107 orthogonal to the x-rays 102.

Figure 2:
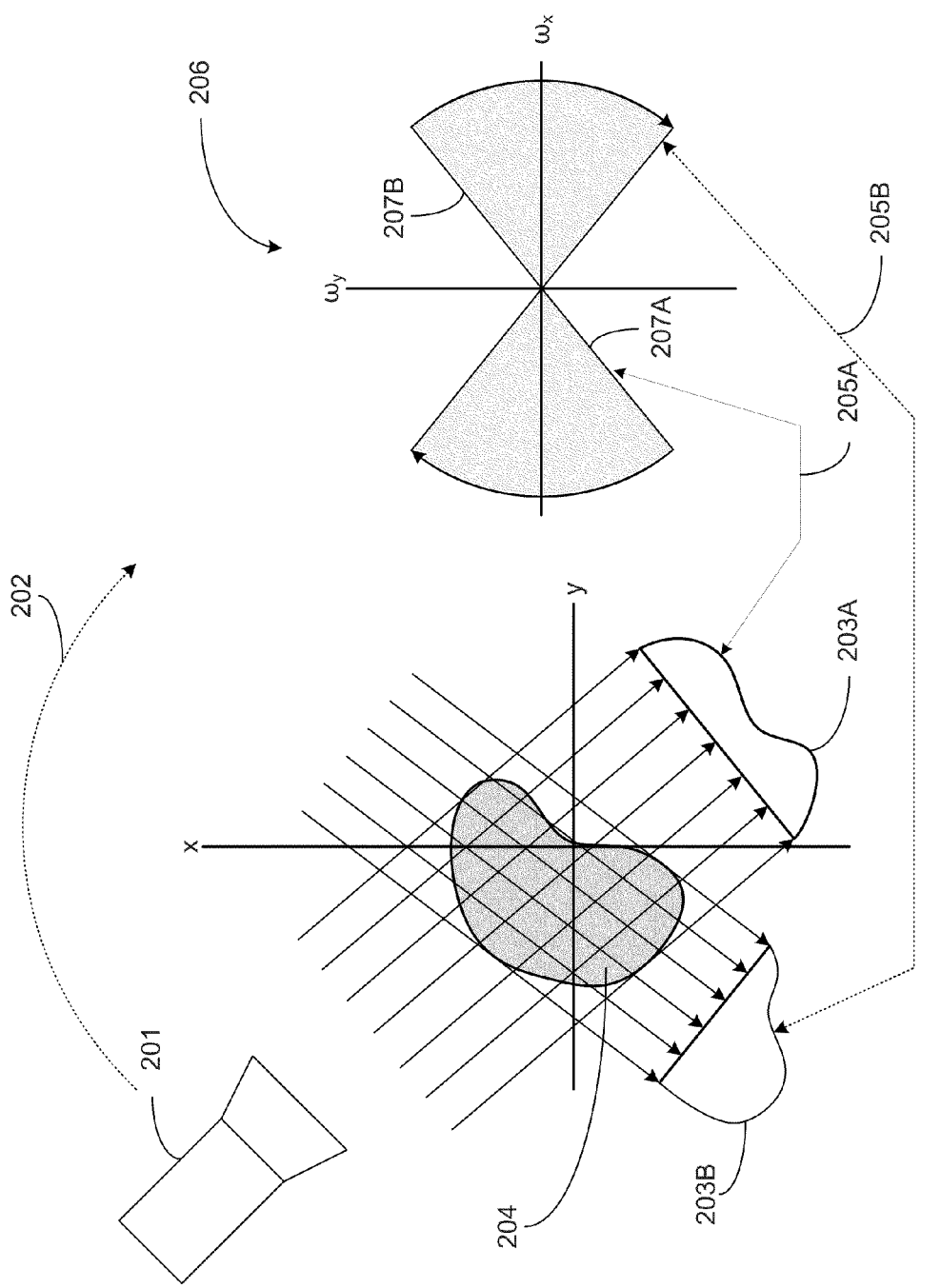
FIG. 2 depicts the rotational movement of an x-ray source.

Referring to FIG. 2, which represents conventional DT, the x-ray source 201 traverses a circular arc 202 and absorption projections 203 are acquired for an object 204 at various points along the arc 202. Each source location results in a projection 203, the Fourier transform 205 of which represents a cross-section of the Fourier transform of the object 204. The plots 207A and 207B of the Fourier transforms 205A and 205B for projections 203A and 203B are used to construct the Fourier space representation 206 of the object 204, as shown at the right side of FIG. 2.

Greater coverage of the source movement arc 202 will result in increased coverage of the Fourier space. When the source movement arc 202 reaches its natural limit of 180°, the sampling of the Fourier space is complete and the object 204 may be exactly reconstructed and the resolution of the DT image will approach that of a CT image. However, such an extensive sampling process is time consuming and may be less than desirable when lesser degrees of coverage are required.

Figure 3:
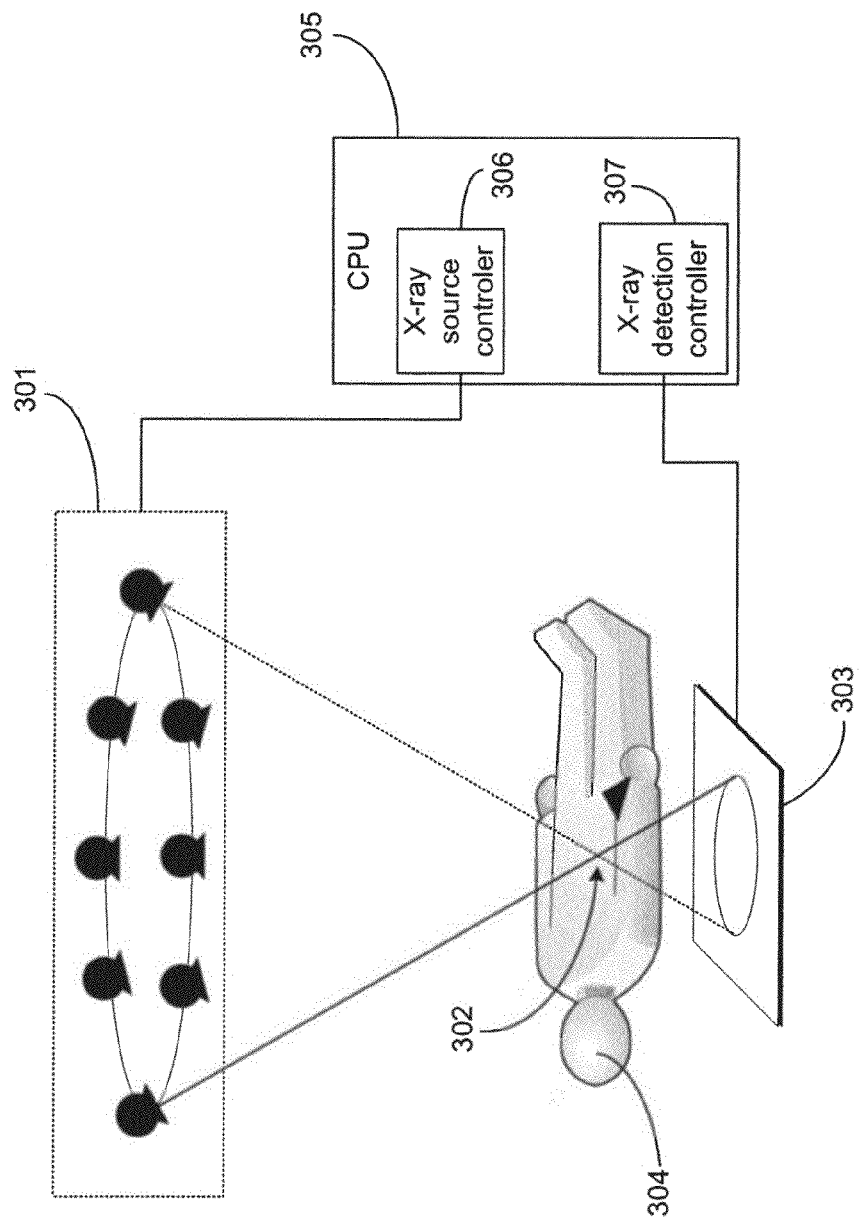
FIG. 3 depicts a tomographic imaging system.

Referring to FIG. 3, a system for obtaining DT images is presented. The system may comprise a plurality of imaging x-ray sources 301 disposed in a fixed relation with respect to one another. Imaging x-ray sources 301 are shown disposed in a ring-shaped configuration, but embodiments are not limited thereto. Each x-ray source 301 is pointed at a common isocenter 302. An x-ray detector 303 may be disposed in a position where the object to be imaged 304 is aligned between the plurality of x-ray sources 301 and the detector 303. The system may further comprise a processing unit 305 including an x-ray control system 306 and an x-ray detection system 307. The x-ray control system 306 may comprise application specific integrated circuitry (ASIC), firmware or software configured to run on a microprocessor to control the firing of the x-ray sources 301. The x-ray detection system 307 may comprise ASIC, firmware or software configured to sample signals from the x-ray detector 303 and carry out tomosynthesis calculations based on those samples.

In some embodiments, each x-ray source of the plurality of statically positioned x-ray sources 301 may be controlled by the x-ray source controller 306 to be fired in a sequential manner resulting in a corresponding tomographic image. Such a methodology allows for the acquisition of radiographic projections from multiple source locations without any physical source movement.

The x-ray sources 301 may comprise carbon nanotube field-emission electron sources. Such electron sources, and their methods of production, are described in the literature, for example in S. Iijimia, *Nature* (London) 354, 56 (1991); W. A. de Heer et al, *Science,* 270, 1179-1180 (1995); and Q. H. Wang et al., *Appl. Phys. Lett.* 70 (24), 3308-3310, Jun. 16, 1997, the contents of which are hereby incorporated by reference. The use of such field-emission electron sources in x-ray tubes of the foregoing type has been found to enable the x-ray tubes to be miniaturized such as to be useful in many medical applications requiring high tube outputs without excessive heating. One feature of such carbon nanotube-enabled x-ray sources is their ability to be switched between enabled and disabled states at very high rates. Such rapid switching allows for frequency modulation of the resulting x-ray images.

Each x-ray source of the plurality of x-ray sources 301 may be switched between enabled and disabled states with a different frequency. For example, sources $S_1$-$S_n$ 301 may be switched at a known frequencies $f_1$-$f_n$ where $f_1 < f_2 < \ldots < f_n$ where $f_n$ is the peak switching frequency. The x-ray detector 303 may be sampled with a frequency greater than $2f_n$ (i.e. the Nyquist frequency) so that a series of images may be acquired from all sources $S_n$ 301 simultaneously. The source switching frequencies $f_1$-$f_n$ may be selected such that no individual switching frequency $f_i$ is a harmonic of any other switching frequency. As such, the image associated with each source may be isolated using Fourier analysis and band-pass filtering techniques such as those commonly used in frequency multiplexing.

Figure 4:
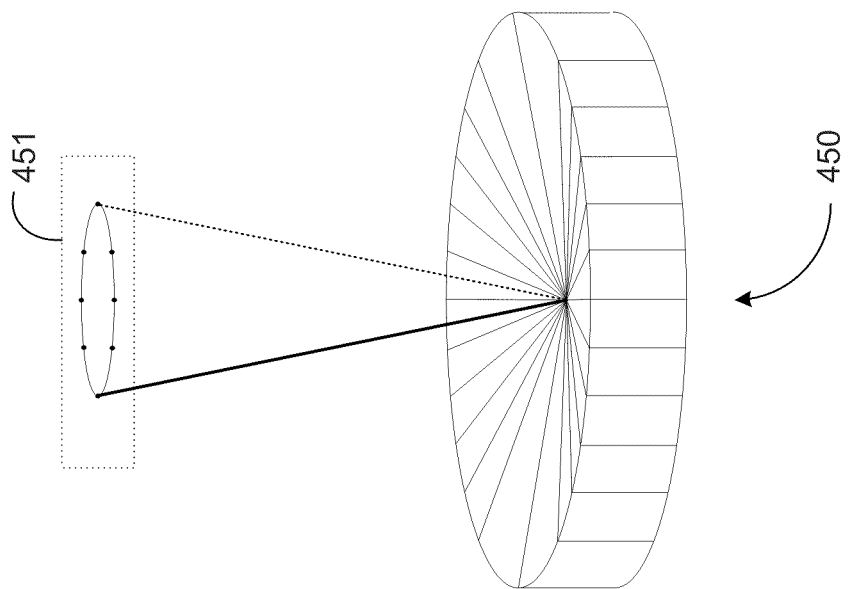
FIG. 4 depicts the Fourier space coverage of a tomographic imaging system.
Figure 4:
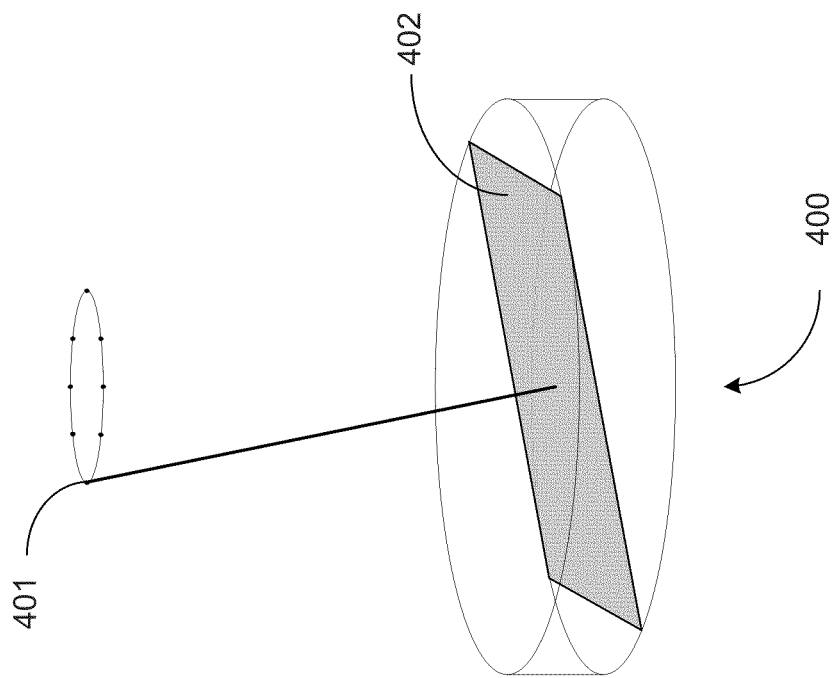

Referring to FIG. 4, a Fourier space sample 400 for a single source 401 and a composite view of the combined Fourier space samples 450 for a plurality of sources 451 in a ring-shaped configuration are presented. Each source position 401 corresponds to one plane 402 in the object Fourier space. Such a ring-shaped configuration results in isotropic sampling of the Fourier space.

Figure 5:
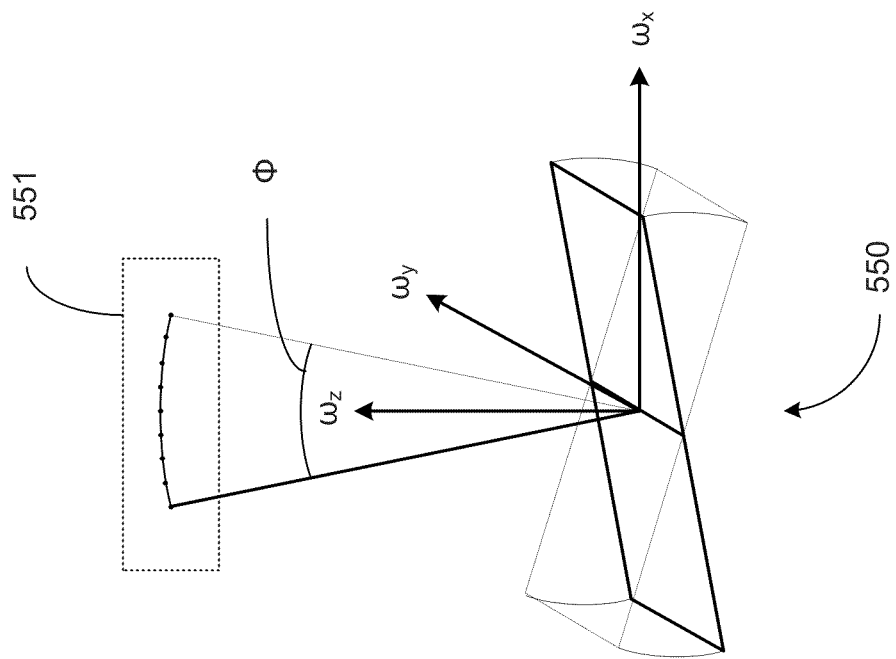
FIG. 5 depicts the Fourier space coverage of various tomographic imaging systems.
Figure 5:
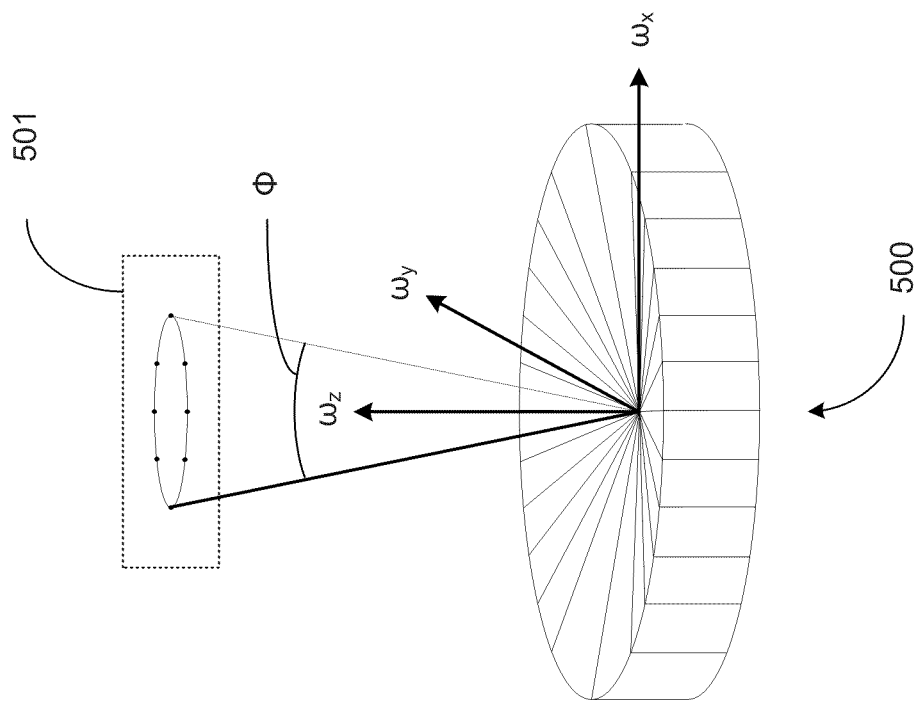

Such sampling characteristics are in contrast to an arc-shaped source configuration. Referring to FIG. 5, the Fourier sampling 500 of a plurality of x-ray sources in a ring-shaped configuration 501 and the Fourier sampling 550 of a plurality of x-ray sources in an arc-shaped configuration 551 are presented. As can be seen, for the configuration 551, higher spatial frequencies along the x-axis will result in better sampling in the z-direction. However, higher spatial frequencies along the y-axis have no effect on sampling in the z-direction. As such, for a given span angle φ, the ring-shaped configuration results in more complete coverage of the Fourier space.

It should be noted that, while the above description has been provided with respect to x-ray sources disposed in a ring-shaped configuration, it is fully contemplated that the x-ray sources may be configured in any shape. Oval, rectangular or irregularly shaped configurations may be used.

Figure 6:
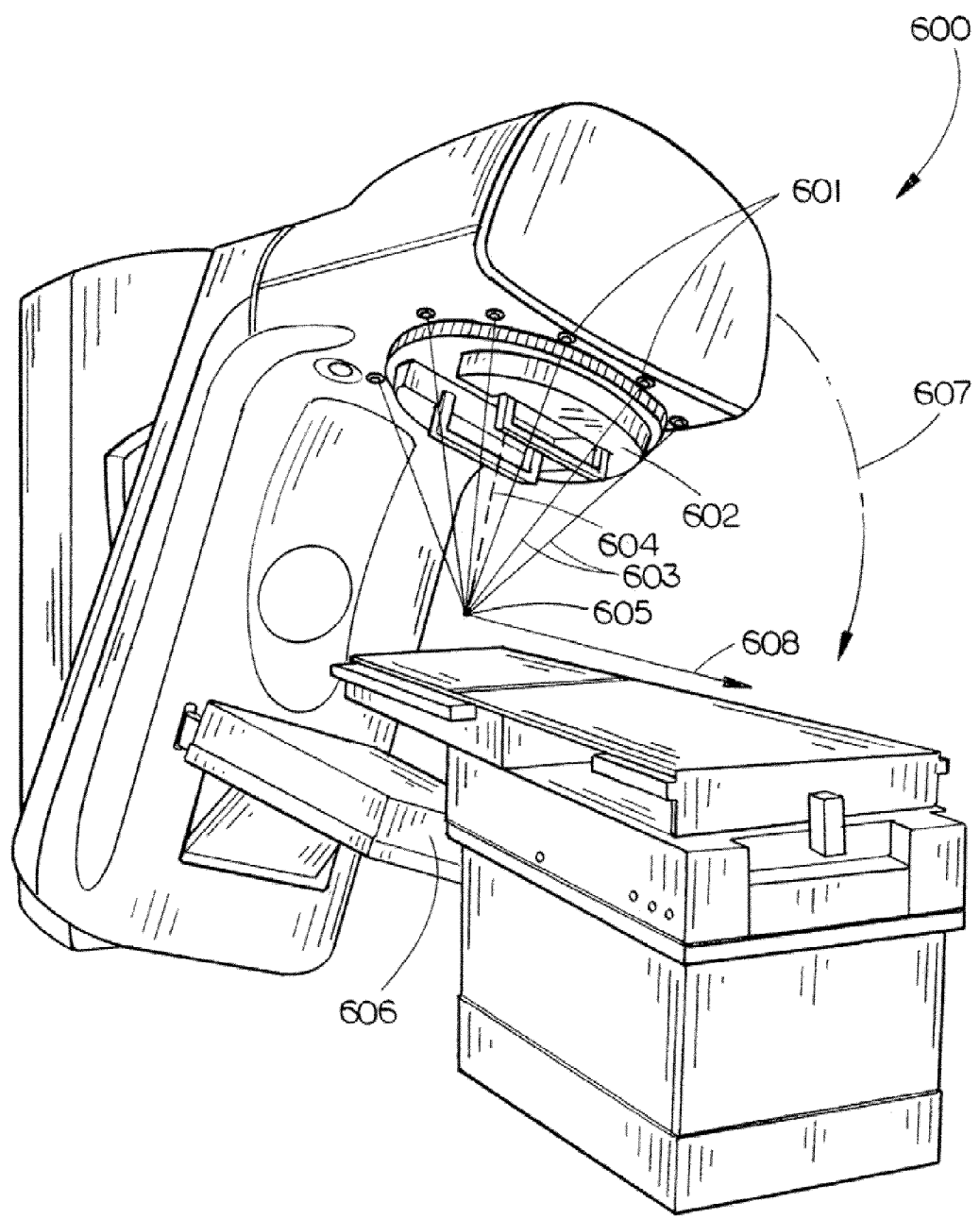
FIG. 6 depicts a tomographic imaging system.

Referring to FIG. 6, a plurality of statically positioned x-ray sources 601 may be disposed in a ring-shaped configuration substantially encircling a therapeutic radiation source 602, such as a linear accelerator (LINAC) or a particle therapy system 600. The x-ray sources 601 and therapeutic radiation source 602 may be aligned such that the x-rays 603 and the therapeutic radiation 604 have a common isocenter 605. Such a configuration allows for optimum imaging quality along the principle axis of the therapeutic beam 604. Additionally, the incorporation of the ring-shaped x-ray sources 601 and the associated imaging detector panel 606 onto a LINAC capable of rotational movement 607 about an axis 608 normal to the therapeutic radiation allows for greater flexibility in imaging orientation.

Figure 7:
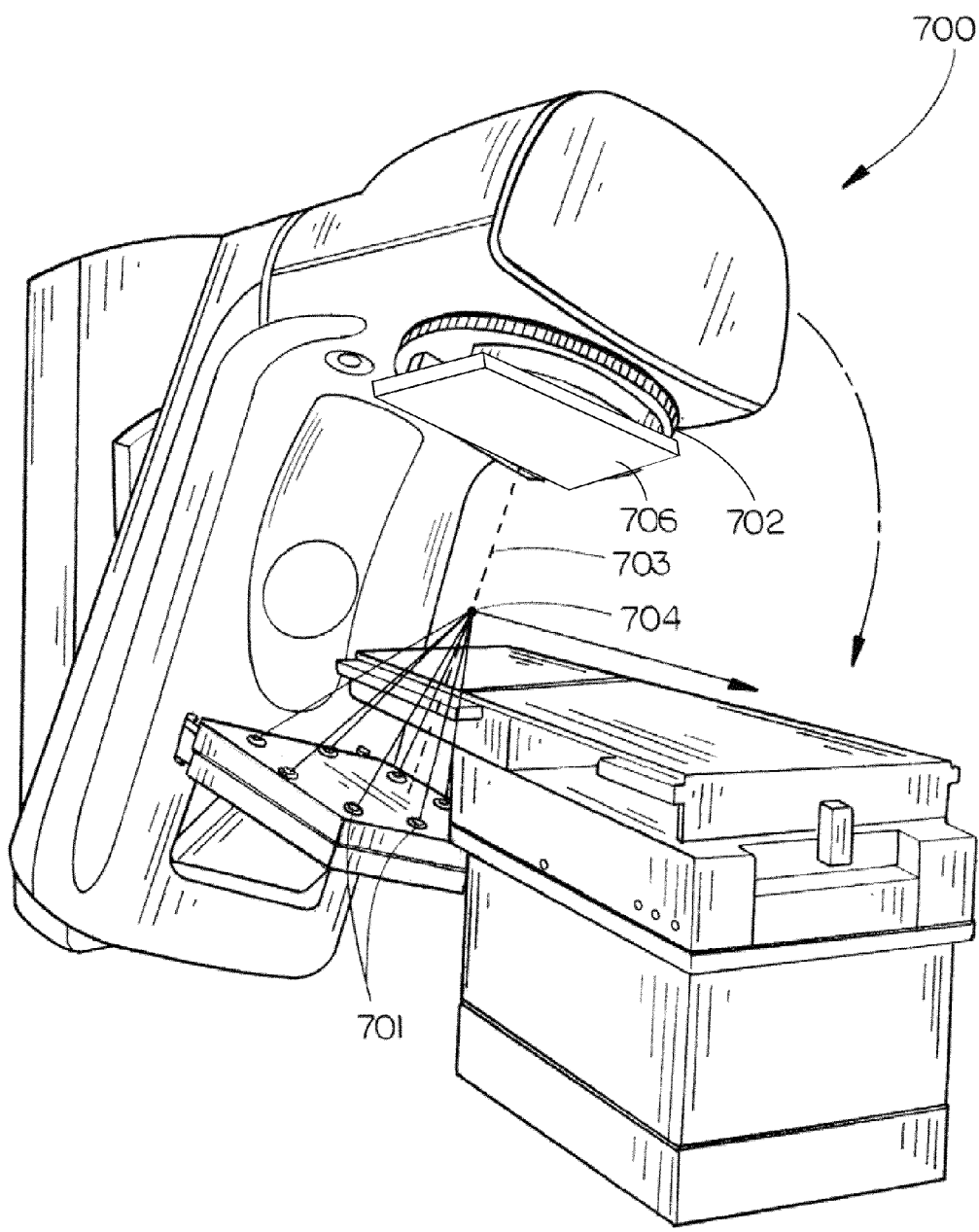
FIG. 7 depicts a tomographic imaging system.

Referring to FIG. 7, a ring of x-ray sources 701 may be placed in a direction substantially opposing a therapeutic radiation source 702 of particle therapy system 700. In this case, an imaging panel 706 will be placed in the path of the therapeutic radiation 703 (i.e. the MV radiation will have to be delivered through the panel). Such a configuration will permit tomographic imaging as described herein during delivery of therapeutic radiation 703. The x-ray sources 701 and therapeutic radiation source 702 may be aligned such that the x-rays from x-ray sources 701 and the therapeutic radiation 703 have a common isocenter 704. As the image detector is in the beam path, the radiation field will have an imprint on the projection images. The effect of the therapeutic beam on the image may be factored out by different method. One such method may include subtracting a mask image resulting from the radiation field (while the X-ray sources are disabled) from the tomographic image obtained using the x-ray sources during a therapy session.

Figure 8:
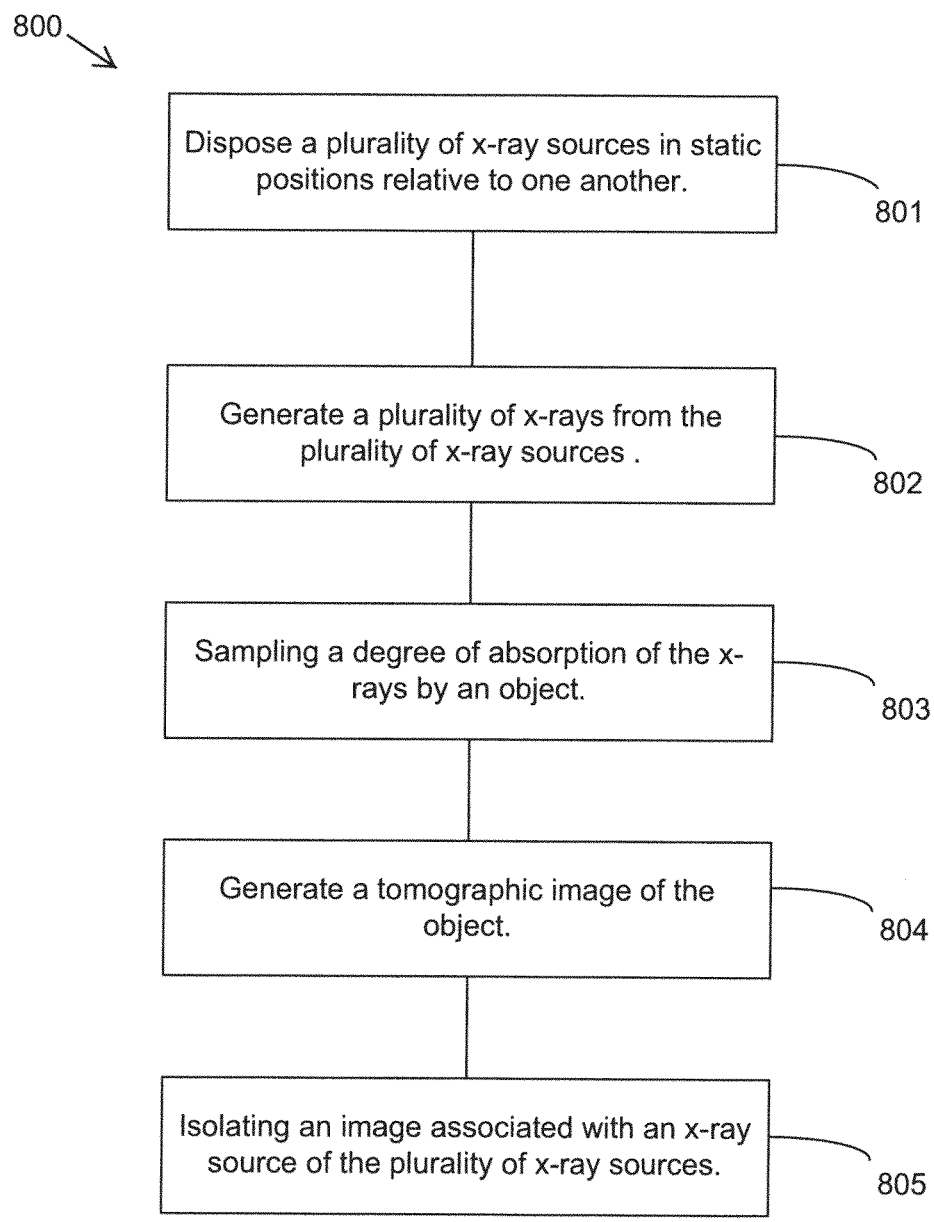
FIG. 8 depicts a method for tomographic imaging.

Referring to FIG. 8, a method 800 for creating a tomographic image is presented. A plurality of x-ray sources may be disposed in static positions with respect to one another at step 801 such that each x-ray source will emit an imaging x-ray toward an object from a different angle. The configuration of the x-ray sources may be a circular, oval, rectangular or any closed shape.

A plurality of x-rays may be emitted from each of the x-ray sources at step 802. The step of emitting the x-rays may further comprise switching each x-ray source between enabled and disabled states. The degree of absorption of the x-rays by an object may be sampled at step 803. Step 803 may comprise acquiring x-ray absorption projections of the object, wherein each of the x-ray absorption projections is associated with an imaging x-ray emitted by a respective one of the plurality of imaging x-ray sources.

In a particular embodiment, the speed of the acquisition of samples at step 803 may be enhanced by modulating the frequencies at which the x-ray sources of the plurality of x-ray sources are be switched at step 802. For example, sources $S_1$-$S_n$ may be switched at a known frequencies $f_1$-$f_n$ where $f_1 < f_2 < \ldots < f_n$ where $f_n$ is the peak switching frequency.

The sampling rate of the absorption of the x-rays 803 must occur less than one half (½) of the readout (sampling) frequency of the imaging panel so that a series of images may be acquired from all sources $S_n$ simultaneously. The source switching frequencies $f_1$-$f_n$ may be selected such that no individual switching frequency $f_i$ is a harmonic of any other switching frequency.

Digital tomosynthesis may be performed at step 804 using the x-ray absorption projections to generate a cross-sectional image of the object. There are a variety of reconstruction methods in the art that may be used for DT reconstruction from the X-ray projection images.

If the sampling at step 803 occurs such that no individual switching frequencies $f_i$ are a harmonic of any other switching frequency, a tomographic image associated with a given x-ray source may be isolated at step 805. Such isolation may be conducted using known Fourier analysis and bandpass filtering techniques.

According to some embodiments, a characteristic of a therapeutic x-ray (e.g., shape, intensity, duration, etc.) to be delivered by the therapeutic radiation source is automatically modified based on the generated cross-sectional image.

Similarly, the steps of the method 800 may be implemented as computer readable instructions which may be stored on a computer readable medium. These computer readable instructions may comprise firmware or software and may be executed by a processing device such as an ASIC or a microprocessor.

It is believed that many of attendant advantages will be understood from the foregoing description, and it will be apparent that various changes may be made in the form, construction, and arrangement of the components thereof without departing from the scope of the appended claims.

What is claimed is:

1. A method comprising:
   emitting a respective imaging x-ray from each of a plurality of imaging x-ray sources disposed in a fixed relation with respect to one another in a closed curve configuration;
   acquiring x-ray absorption projections of an object, each of the x-ray absorption projections associated with an imaging x-ray emitted by a respective one of the plurality of imaging x-ray sources;
   performing digital tomosynthesis using the x-ray absorption projections to generate a cross-sectional image of the object; and
   delivering a therapeutic x-ray from a therapeutic radiation source to the object,
   wherein each of the plurality of imaging x-ray sources is disposed in a fixed relation with respect to the therapeutic radiation source, and wherein the plurality of imaging x-ray sources comprise carbon nanotube field-emission electron sources.

2. A method according to claim 1, wherein the therapeutic x-ray is delivered while the x-ray absorption projections are acquired and while digital tomosynthesis is performed.

3. A method according to claim 1, further comprising:
   automatically modify a characteristic of the therapeutic x-ray to be delivered by the therapeutic radiation source based on the cross-sectional image.

4. A method according to claim 1, wherein the plurality of imaging x-ray sources are disposed in a ring-shaped configuration.

5. A method according to claim 1, wherein the plurality of imaging x-ray sources remain stationary with respect to the therapeutic radiation source during acquisition of the x-ray absorption projections.

6. An apparatus comprising:
   a plurality of imaging x-ray sources disposed in a fixed relation with respect to one another in a closed curve configuration, each of the plurality of imaging x-ray sources to emit a respective imaging x-ray;
   an x-ray detector to acquire x-ray absorption projections of an object, each of the x-ray absorption projections associated with an imaging x-ray emitted by a respective one of the plurality of imaging x-ray sources;
   a processor to perform digital tomosynthesis using the x-ray absorption projections to generate a cross-sectional image of the object; and
   a therapeutic radiation source to deliver a therapeutic x-ray, wherein each of the plurality of imaging x-ray sources is disposed in a fixed relation with respect to the therapeutic radiation source, and wherein the plurality of imaging x-ray sources comprise carbon nanotube field-emission electron sources.

7. An apparatus according to claim 6, wherein the x-ray detector is disposed between the plurality of imaging x-ray sources and the therapeutic radiation source.

8. An apparatus according to claim 6, wherein the plurality of imaging x-ray sources are disposed in a ring-shaped configuration.

9. An apparatus according to claim 6, wherein the therapeutic radiation source is to deliver the therapeutic x-ray while the x-ray detector acquires the x-ray absorption projections and while the processor performs digital tomosynthesis using the x-ray absorption projections to generate the cross-sectional image.

10. An apparatus according to claim 6, the processor further to:
    automatically modify a characteristic of the therapeutic x-ray to be delivered by the therapeutic radiation source based on the cross-sectional image.

11. An apparatus according to claim 6, wherein the plurality of imaging x-ray sources are to remain stationary with respect to the therapeutic radiation source during acquisition of the x-ray absorption projections.

* * * * *